United States Patent
Samset

(10) Patent No.: US 10,588,605 B2
(45) Date of Patent: Mar. 17, 2020

(54) METHODS AND SYSTEMS FOR SEGMENTING A STRUCTURE IN MEDICAL IMAGES

(71) Applicant: General Electric Company, Schenectady, NY (US)

(72) Inventor: Eigil Samset, Horten (NO)

(73) Assignee: General Electric Company, Schenectady, NY (US)

( * ) Notice: Subject to any disclaimer, the term of this patent is extended or adjusted under 35 U.S.C. 154(b) by 1177 days.

(21) Appl. No.: 14/923,952

(22) Filed: Oct. 27, 2015

(65) Prior Publication Data
US 2017/0112473 A1    Apr. 27, 2017

(51) Int. Cl.
*A61B 8/08* (2006.01)
*A61B 8/00* (2006.01)
*A61B 8/06* (2006.01)

(52) U.S. Cl.
CPC .............. *A61B 8/5246* (2013.01); *A61B 8/06* (2013.01); *A61B 8/0883* (2013.01); *A61B 8/4483* (2013.01); *A61B 8/483* (2013.01); *A61B 8/485* (2013.01); *A61B 8/486* (2013.01); *A61B 8/488* (2013.01); *A61B 8/5207* (2013.01)

(58) Field of Classification Search
CPC ........... A61B 8/06; A61B 8/483; A61B 8/485; A61B 8/486; A61B 8/488; A61B 8/0883; A61B 8/4483; A61B 8/5207; A61B 8/5246
See application file for complete search history.

(56) References Cited

U.S. PATENT DOCUMENTS

| 5,980,459 | A | 11/1999 | Chiao et al. | |
|---|---|---|---|---|
| 6,322,509 | B1 * | 11/2001 | Pan | A61B 5/1075 600/443 |
| 2009/0226058 | A1 * | 9/2009 | Li | G06T 7/11 382/128 |

(Continued)

FOREIGN PATENT DOCUMENTS

WO    WO-2015189160 A1 * 12/2015    ........... A61B 8/0883

OTHER PUBLICATIONS

Fredrik Orderud, "Real-time 3D Segmentation of the Left Ventricle Using Deformable Subdivision Surfaces", iEEE, 2008, pp. 1-8.

*Primary Examiner* — Boniface N Nganga
(74) *Attorney, Agent, or Firm* — Dean D. Small; The Small Patent Law Group, LLC

(57) ABSTRACT

Methods and systems for segmenting structures in medical images are provided. The methods and systems drive a plurality of transducer element, and collect receive signals from the transducer array at a receive beamformer to form beam summed signals. The methods and systems generate a first ultrasound image of a region of interest (ROI) having tissue elements and blood elements, and generate a second ultrasound image of the ROI having tissue elements and blood elements. The tissue elements of the first ultrasound image having a higher intensity than the blood elements. The blood elements of the second ultrasound image having a higher intensity than the tissue elements. The methods and systems further perform segmentation by simultaneously applying edge detection on the first and second ultrasound images for the ROI.

21 Claims, 11 Drawing Sheets

(56) References Cited

U.S. PATENT DOCUMENTS

2011/0208056 A1* 8/2011 Datta .................. A61B 8/06
                                                    600/441
2013/0245441 A1* 9/2013 Datta .................. A61B 8/13
                                                    600/438

* cited by examiner

METHODS AND SYSTEMS FOR SEGMENTING A STRUCTURE IN MEDICAL IMAGES

FIELD

Embodiments described herein generally relate to segmenting structure in medical images, and more particularly to segmenting a region of interest based on a B-mode ultrasound image and a B-flow ultrasound image.

BACKGROUND OF THE INVENTION

Conventional ultrasound imaging systems usually include ultrasound scanning devices, such as ultrasound probes having transducers that are connected to an ultrasound system to control the acquisition of ultrasound data during an examination (e.g., ultrasound scan) by a user to acquire one or more ultrasound images or videos (e.g., imaging the volume or body) of a patient such as a B-mode image. A brightness of pixels within the B-mode image is based on an intensity of echo signals represented by the ultrasound data, which correspond to structures of tissue within the patient. Diagnostic tools of conventional ultrasound imaging systems allow users to segment selected structures within the B-mode image based on the relative brightness of the pixels.

However, B-mode images are prone to drop-outs, shadowing, noise, and/or other acoustical artifacts that affect accuracy in segmenting structures within B-mode images requiring statistical modeling.

BRIEF DESCRIPTION OF THE INVENTION

In one embodiment, an ultrasound imaging system is provided. The ultrasound imaging system may include a transducer array. The transducer array includes a plurality of transducer elements. The ultrasound imaging system also includes a transmit circuit to drive the transducer array, and a receive beamformer to collect receive signals from the transducer array forming beam summed signals. The ultrasound imaging system may also include one or more processors and a memory for storing programmed instructions. The one or more processors execute the programmed instruction by performing multiple operations. The one or more processors may generate a first ultrasound image of a region of interest (ROI) having tissue elements and blood elements. The tissue elements of the first ultrasound image having a higher intensity than the blood elements. The one or more processors may generate a second ultrasound image of the ROI having tissue elements and blood elements. The blood elements of the second ultrasound image having a higher intensity than the tissue elements. The one or more processors may further perform segmentation by simultaneously applying edge detection on the first and second ultrasound images for the ROI.

In another embodiment, a method for segmenting a structure is provided. The method may include driving a plurality of transducer elements and collecting receive signals from the transducer array at a receive beamformer to form beam summed signals. The method may further generate a first ultrasound image of a region of interest (ROI) having tissue elements and blood elements. The tissue elements of the first ultrasound image having a higher intensity than the blood elements. The method may further generate a second ultrasound image of the ROI having tissue elements and blood elements. The blood elements of the second ultrasound image having a higher intensity than the tissue elements. Additionally, the method may perform segmentation by simultaneously applying edge detection on the first and second ultrasound images for the ROI.

In another embodiment, a tangible and non-transitory computer readable medium may include one or more computer software modules configured to direct one or more processors. The one or more computer software modules may be configured to direct the one or more processors to drive a plurality of transducer elements, and collect receive signals from the transducer array at a receive beamformer to form beam summed signals. The one or more computer software modules may further be configured to direct the one or more processors to generate a first ultrasound image of a region of interest (ROI) having tissue elements and blood elements. The tissue elements of the first ultrasound image having a higher intensity than the blood elements. The one or more computer software modules may further be configured to direct the one or more processors to generate a second ultrasound image of the ROI having tissue elements and blood elements. The blood elements of the second ultrasound image having a higher intensity than the tissue elements. Further, the one or more computer software modules may be configured to direct the one or more processors to perform segmentation by simultaneously applying edge detection on the first and second ultrasound images for the ROI.

DETAILED DESCRIPTION OF THE INVENTION

Figure 1:
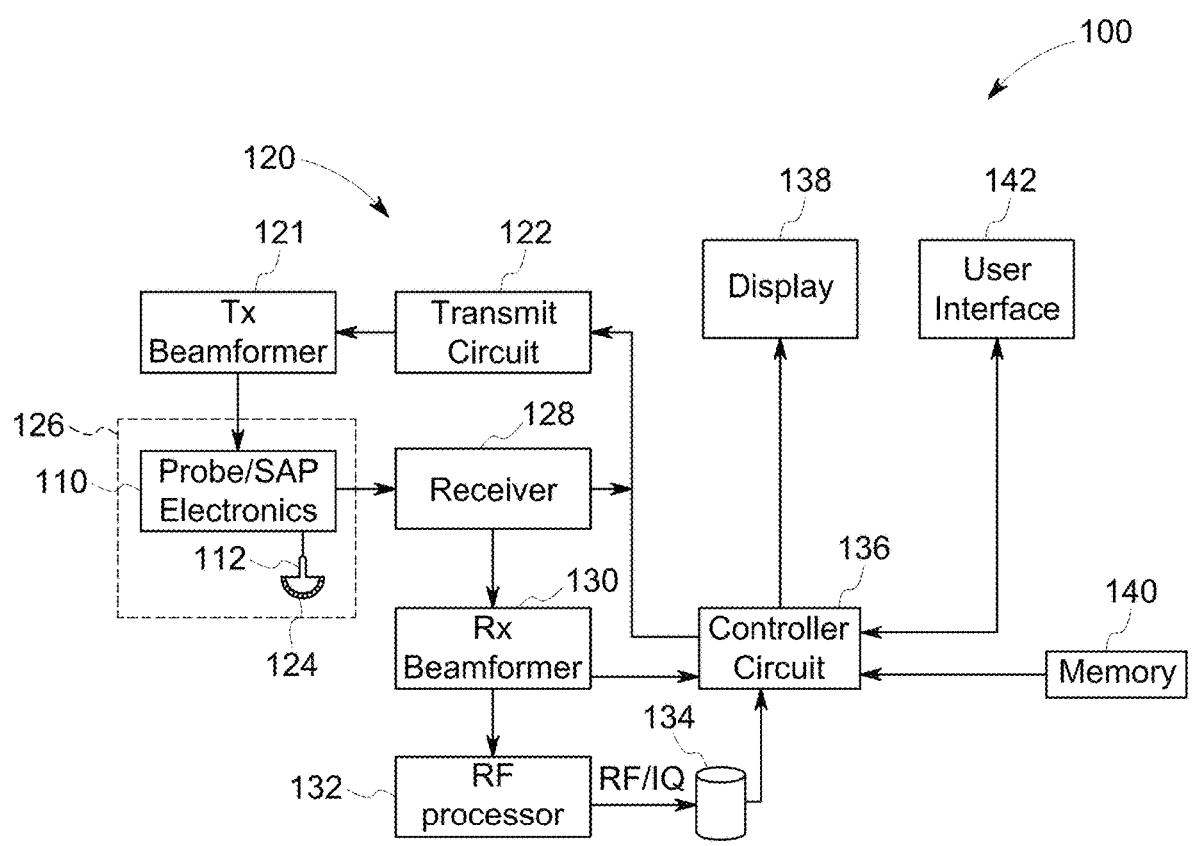
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods which combine measurements in a B-mode ultrasound image with measurement made using coded excitation for a B-flow ultrasound image. The B-flow ultrasound image provides flow information, such as blood flow or movement of tissue. Various embodiments simultaneously apply an edge detection to the B-mode and B-flow ultrasound images to track an anatomical shape, such as a cardiac structure (e.g., left ventricle), corresponding to a region of interest. For example, the edge detection of the B-flow image may identify a blood-tissue interface (e.g., endocardium) of the cardiac structure. The edge detections of the B-mode and B-flow ultrasound images may be combined and/or assimilated creating a more accurate set of measurements for segmentation of the anatomical shape relative to only edge detection of the B-mode ultrasound image.

A technical effect of at least one embodiment includes a more robust segmentation result for quantitative analysis of anatomical structures.

FIG. 1 is a schematic diagram of a diagnostic medical imaging system, specifically, an ultrasound imaging system 100. The ultrasound imaging system 100 includes an ultrasound probe 126 having a transmit circuit 122 and probe/SAP electronics 110. The ultrasound probe 126 may be configured to acquire ultrasound data or information from a region of interest (e.g., organ, cardiac structure, blood vessel) of the patient. The ultrasound probe 126 is communicatively coupled to the controller circuit 136 via the transmit circuit 122. The transmit circuit 122 transmits a signal (e.g., coded excitation, uncoded excitation) to a transmit beamformer 121 based on acquisition settings received by the user. The signal transmitted by the transmit circuit 122 in turn drives the transducer elements 124 within the transducer array 112. The transducer elements 124 emit pulsed ultrasonic signals into a patient (e.g., a body). A variety of a geometries and configurations may be used for the array 112. Further, the array 112 of transducer elements 124 may be provided as part of, for example, different types of ultrasound probes.

The acquisition settings may define an amplitude, pulse width, frequency, and/or the like of the ultrasonic pulses emitted by the transducer elements 124. The acquisition settings may be adjusted by the user by selecting a gain setting, power, time gain compensation (TGC), resolution, and/or the like from a user interface 142.

The transducer elements 124, for example piezoelectric crystals, emit pulsed ultrasonic signals into a body (e.g., patient) or volume corresponding to the acquisition settings. The ultrasonic signals may include, for example, one or more reference pulses, one or more pushing pulses (e.g., shear-waves), and/or one or more tracking pulses. At least a portion of the pulsed ultrasonic signals back-scatter from a region of interest (ROI) (e.g., breast tissues, liver tissues, cardiac tissues, prostate tissues, and the like) to produce echoes. The echoes are delayed in time according to a depth, and are received by the transducer elements 124 within the transducer array 112. The ultrasonic signals may be used for imaging, for generating and/or tracking shear-waves, for measuring differences in compression displacement of the tissue (e.g., strain), and/or for therapy, among other uses. For example, the probe 126 may deliver coded and uncoded excitation pulses.

Coded Excitation is the transmission of long encoded pulse sequences and decoding (e.g., filtering) of the received signals in order to improve image SNR and/or resolution. The energy contained in a long transmit pulse sequence is compressed into a short time interval on receive by virtue of the code. Coded excitation and filtering techniques are described in, for example, U.S. Pat. No. 5,980,459, entitled "ULTRASOUND IMAGING USING CODED EXCITATION ON TRANSMIT AND SELECTIVE FILTERING OF FUNDAMENTAL AND (SUB)HARMONIC SIGNALS ON RECEIVE" and U.S. Pat. No. 6,210,332, entitled, "METHOD AND APPARATUS FOR FLOW IMAGING USING CODED EXCITATION," both of which are expressly incorporated herein by reference.

The transducer array 112 may have a variety of array geometries and configurations for the transducer elements 124 which may be provided as part of, for example, different types of ultrasound probes 126. The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical receive signals which may be received by a receiver 128. The electrical receive signals representing the received echoes are passed through a receive beamformer 130. Generally, the receive beamformer 130 collects the electrical receive signals from the transducer elements 124 to form beam summed signals based on the electrical receive signals. For example, the receive beamformer 130 imparts a time delay and weight to each of the electrical receive signals, which are summed by the receive beamformer 130 to form the beam summed signals. The receive beamformer 130 may output the beam summed signals to the controller circuit 136.

The receive beamformer 130 may include dedicated hardware, such as an application specific integrated circuits. Additionally or alternatively, the receive beamformer 130 may include one or more processors, a central controller circuit (CPU), or any other electronic component capable of processing inputted data according to specific logical instructions. Additionally or alternatively, the receive beamformer 130 may execute instructions stored on a tangible and non-transitory computer readable medium (e.g., the memory 140) for beamforming calculations (e.g., software beamforming) using any suitable beamforming method, for example, adaptive beamforming, synthetic transmit focus, aberration correction, synthetic aperture, clutter reduction and/or adaptive noise control, and/or the like.

Additionally or alternatively, the receive beamformer 130 may perform beamforming on the electrical receive signals and outputs to a radio frequency (RF) signal. The RF signal is then provided to an RF processor 132 that processes the RF signal. The RF processor 132 may generate different ultrasound image data types, e.g. B-mode, color Doppler (velocity/power/variance), tissue Doppler (velocity), and Doppler energy, for multiple scan planes or different scanning patterns. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, on the memory 134.

Alternatively, the RF processor 132 may include a complex demodulator (not shown) that demodulates the RF signal to form IQ data pairs representative of the echo signals. The RF or IQ signal data may then be provided directly to a memory 134 for storage (e.g., temporary storage).

The controller circuit 136 may be configured to process the acquired ultrasound data (e.g., RF signal data, beam summed signal, IQ data pairs) and prepare frames of ultrasound image data for display on the display 138. The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140).

The controller circuit 136 is configured to perform one or more processing operations according to a plurality of selectable ultrasound modalities on the acquired ultrasound data, adjust or define the ultrasonic pulses emitted from the transducer elements 124, adjust one or more image display settings of components (e.g., ultrasound images, interface components) displayed on the display 138, and other operations as described herein. Acquired ultrasound data may be processed in real-time by the controller circuit 136 during a scanning or therapy session as the echo signals are received. Additionally or alternatively, the ultrasound data may be stored temporarily on the memory 134 during a scanning session and processed in less than real-time in a live or off-line operation.

The ultrasound imaging system 100 may include a memory 140 for storing processed frames of acquired ultrasound data that are not scheduled to be displayed immediately or to store post-processed images (e.g., shear-wave images, strain images), firmware or software corresponding to, for example, a graphical user interface, one or more default image display settings, and/or the like. The memory device 140 may be a tangible and non-transitory computer readable medium such as flash memory, RAM, ROM, EEPROM, and/or the like.

One or both of the memory 134 and 140 may store 3D ultrasound image data sets of the ultrasound data, where such 3D ultrasound image data sets are accessed to present 2D and 3D images. For example, a 3D ultrasound image data set may be mapped into the corresponding memory 134 or 140, as well as one or more reference planes. The processing of the ultrasound data, including the ultrasound image data sets, may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored on the memory 134 or 140 or currently being acquired, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142.

For example, a portion of the user interface 142 may correspond to a graphical user interface (GUI) generated by the controller circuit 136 shown on the display. The GUI may include one or more interface components that may be selected, manipulated, and/or activated by the user operating the user interface 142 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 100 performed by the controller circuit 136.

Figure 2:
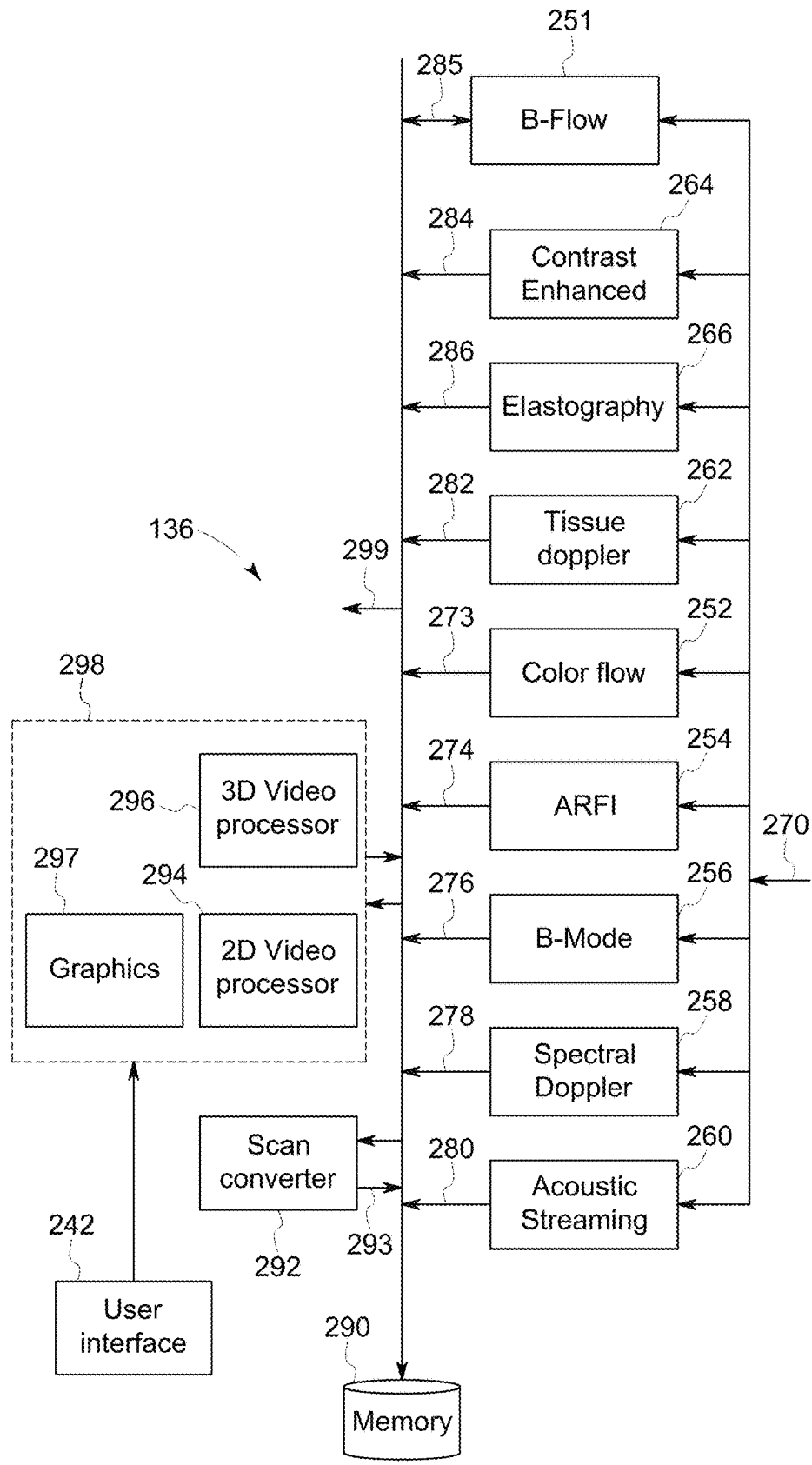
FIG. 2 is an illustration of a simplified block diagram of a controller circuit of the ultrasound imaging system of FIG. 1, in accordance with an embodiment.

FIG. 2 is an exemplary block diagram of the controller circuit 136. The controller circuit 136 is illustrated in FIG. 2 conceptually as a collection of circuits and/or software modules, but may be implemented utilizing any combination of dedicated hardware boards, DSPs, one or more processors, FPGAs, ASICs, a tangible and non-transitory computer readable medium configured to direct one or more processors, and/or the like.

The circuits 251-266 (e.g., dedicated hardware, microprocessors, software modules) perform mid-processor operations representing one or more visual diagnostics, operations, data manipulation, and/or the like of the ultrasound imaging system 100. The circuits 251-266 may be controlled by the controller circuit 136. The controller circuit 136 may receive ultrasound data 270 (e.g., beam summed signals, RF signals, IQ data pairs) in one of several forms. In the embodiment of FIG. 2, the received ultrasound data 270 may constitute IQ data pairs representing the real and imaginary components associated with each data sample of the digitized signals. The IQ data pairs are provided to one or more circuits, for example, a B-flow circuit 251, a color-flow circuit 252, an acoustic radiation force imaging (ARFI) circuit 254, a B-mode circuit 256, a spectral Doppler circuit 258, an acoustic streaming circuit 260, a tissue Doppler circuit 262, a contrast-enhanced circuit 264, and an electrography circuit 266. Other circuits may be included, such as an M-mode circuit, power Doppler circuit, among others. However, embodiments described herein are not limited to processing IQ data pairs. For example, processing may be done with RF data and/or using other methods. Furthermore, data may be processed through multiple circuits.

Each of circuits 251-266 is configured to process the IQ data pairs in a corresponding manner to generate, respectively, B-flow data 285, color-flow data 273, ARFI data 274, B-mode data 276, spectral Doppler data 278, acoustic streaming data 280, tissue Doppler data 282, contrast imaging data 284 (e.g., ROI data acquisition location), electrography data 286 (e.g., strain data, shear-wave data), among others, all of which may be stored in a memory 290 (or the memory 140 shown in FIG. 1) temporarily before subsequent processing. The data 273-286 may be stored, for example, as sets of vector data values, where each set defines an individual ultrasound image frame. The vector data values are generally organized based on the polar coordinate system.

A scan converter circuit 292 accesses and obtains from the memory 290 the vector data values associated with an image frame and converts the set of vector data values to Cartesian coordinates to generate an ultrasound image frame 293 formatted for display. The ultrasound image frames 293 generated by the scan converter circuit 292 may be provided back to the memory 290 for subsequent processing or may be provided to the memory 134 or the memory 140. Once the scan converter circuit 292 generates the ultrasound image frames 293 associated with the data, the image frames may be stored in the memory 290 or communicated over a bus 299 to a database (not shown), the memory 140, and/or to other processors (not shown).

The display circuit 298 accesses and obtains one or more of the image frames from the memory 290 and/or the memory 140 over the bus 299 to display the images onto the display 138. The display circuit 298 receives user input from the user interface 142 selecting one or image frames to be displayed that are stored on memory (e.g., the memory 290) and/or selecting a display layout or configuration for the image frames.

The display circuit 298 may include a 2D video processor circuit 294. The 2D video processor circuit 294 may be used to combine one or more of the frames generated from the different types of ultrasound information. Successive frames of images may be stored as a cine loop (4D images) in the memory 290 or memory 140. The cine loop represents a first in, first out circular image buffer to capture image data that is displayed in real-time to the user. The user may freeze the cine loop by entering a freeze command at the user interface 142.

The display circuit 298 may include a 3D processor circuit 296. The 3D processor circuit 296 may access the memory 290 to obtain spatially consecutive groups of ultrasound image frames and to generate three-dimensional image representations thereof, such as through volume rendering or surface rendering algorithms as are known. The three-dimensional images may be generated utilizing various imaging techniques, such as ray-casting, maximum intensity pixel projection and the like.

The display circuit 298 may include a graphic circuit 297. The graphic circuit 297 may access the memory 290 to obtain groups of ultrasound image frames and the ROI data acquisition locations that have been stored or that are currently being acquired. The graphic circuit 297 may generate images that include the images of the ROI and a graphical representation positioned (e.g., overlaid) onto the images of the ROI. The graphical representation may represent an outline of a treatment space, the focal point or region of the therapy beam, a path taken by the focal region within the treatment space, a probe used during the session, the ROI data acquisition location, and the like. Graphical representations may also be used to indicate the progress of the therapy session. The graphical representations may be generated using a saved graphical image or drawing (e.g., computer graphic generated drawing), or the graphical representation may be directly drawn by the user onto the image using a GUI of the user interface 142.

Figure 3:
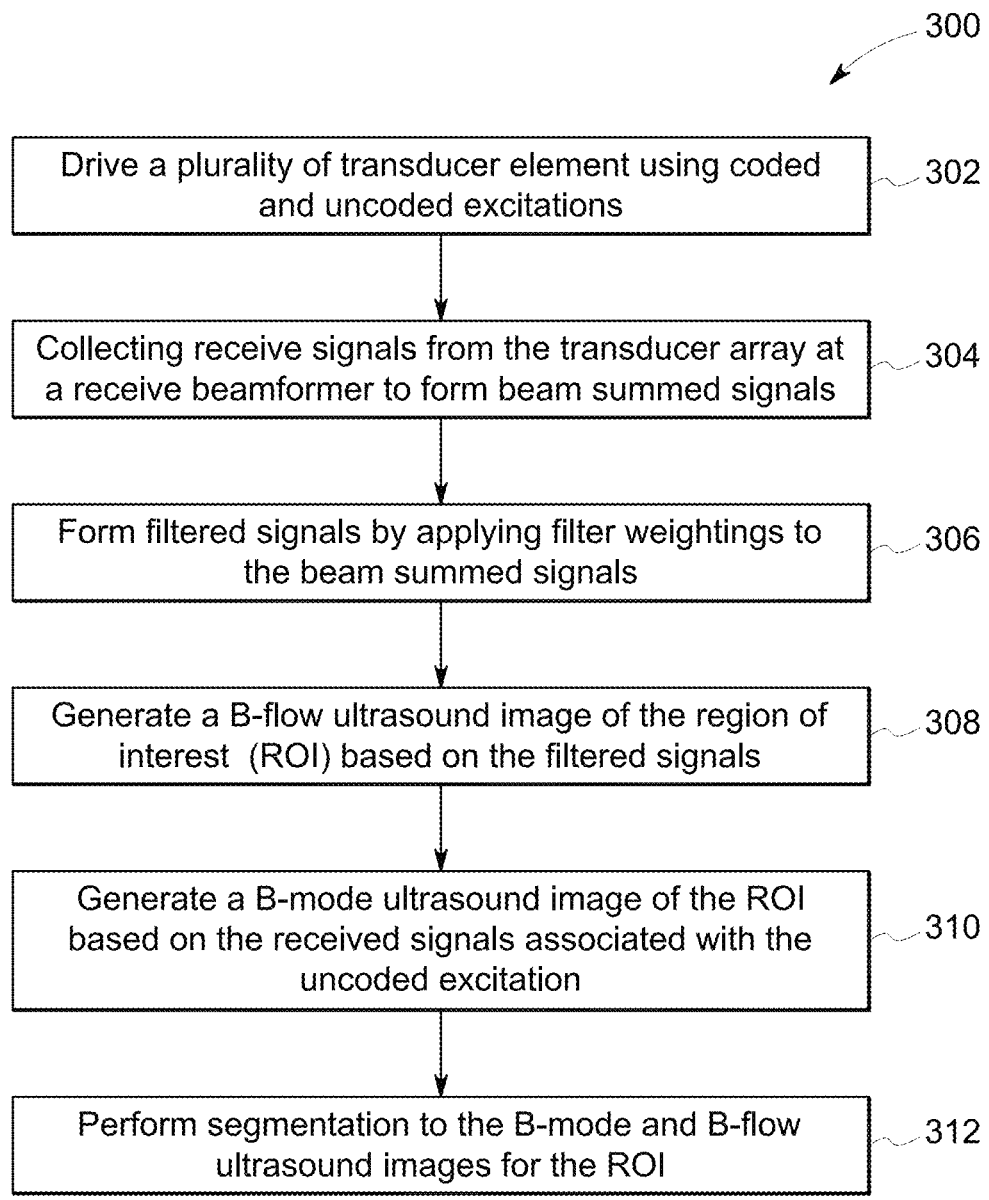
FIG. 3 illustrates a flowchart of a method for segmenting a structure from a first and second ultrasound image, in accordance with an embodiment.

In connection with FIG. 3, the user may select an interface component to perform segmentation of an ROI from two ultrasound images via the user interface 142.

FIG. 3 illustrates a flowchart of a method 300 for segmenting a structure, such as a cardiac structure corresponding to a ROI, from two ultrasound images in accordance with various embodiments described herein. The method 300, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms or software modules stored in memory to direct hardware (e.g., one or more processors) to perform one or more operations described herein. It should be noted, other methods may be used, in accordance with embodiments herein.

One or more methods may (i) drive a plurality of transducer elements; (ii) collect receive signals from the transducer array at a receive beamformer to form beam summed signals; (iii) generate a first ultrasound image of a region of interest (ROI) having tissue elements and blood elements; (iv) generate a second ultrasound image of the ROI having tissue elements and blood elements; and (v) perform segmentation by simultaneously applying edge detection on the first and second ultrasound images for the ROI.

Beginning at 302, a transmit circuit 122 may drive a plurality of transducer elements 124, for example, using coded excitations or coded and uncoded excitations. For example, the controller circuit 136 may instruct the ultrasound probe 126 to switch between coded and uncoded excitations during predetermined acquisition time periods. Optionally, the uncoded excitations pulses may be interleaved and/or followed by the coded excitations. During the coded excitation, the transmit circuit 122, directed by the controller circuit 136, may drive a pulse N times to each transducer element 124. The pulses may correspond to a coded waveform formed by the transmit circuit 122 according to a predefined transmit sequence stored on the memory 140, which is selected by the controller circuit 136. For example, at a first transmit firing (e.g., N=1), the transducer elements 124 are pulsed in accordance with a first transmit code, and at a second transmit firing (e.g., N=2) the transducer elements 124 are pulsed in accordance with a second transmit code having a different phase (e.g., biphasic) with respect to the first transmit code. Optionally, the second transmit code may have a different amplitude with respect to the first transmit code. The controller circuit 136 may select the predefined transmit sequence from a plurality of candidate predefined transmit sequences stored on the memory 140 based on the acquisition settings received by the controller circuit 136 from selections of one or more interface components (e.g., selectable icons, drop-down menus) via the user interface 142.

The transmit beamformer 121 may direct or steer the pulses for each transmit firing at a desired transmit focal position by the transducer elements 124 corresponding to a portion of the ROI. For example, the transmit beamformer 121 may impart time delays to the respective pulses produced by the transmit circuit 122 in response to the transmit sequence from memory 140. The controller circuit 136 may adjust the time delays by the transmit beamformer 121 to focus the pulses emitted by the transducer elements 124 at one or more desired transmit focal positions of the ROI. The N pulses are transmitted to the one or more focal positions with a specified pulse repetition interval (PRI).

At 304, the receive beamformer 130 may collect receive signals from the transducer array 112 to form beam summed signals based on the receive signals. For example, the transducer elements 124 may acquire or receive echo signals in response to the coded and uncoded excitations at 302. The transducer elements 124 may output the received echo signals via the probe/SAP electronics 110 to the receiver 128, which passes the received echo signals to the receive beamformer 130. Based on a direction of the pulses (e.g., corresponding to the focal position), steered by the transmit beamformer 121, the receive beamformer 130 may impart focus time delays to the received echo signals, which are summed by the receive beamformer 130 to form corresponding beam summed signals. For example, each of the beam summed signals indicate a total ultrasonic energy reflected from each of the N transmit firings of the coded excitations focused at a particular transmit focal position.

At 306, the controller circuit 136 may form filtered signals by applying filter weightings to the beam summed signals. For example, the beam summed signals may be included in the ultrasound data 270 (FIG. 2) received by the B-flow circuit 251 as the ultrasound data 270. The B-flow circuit 251 may include a filter for filtering across the N transmit firings. Based thereon, the B-flow circuit 251 supplies filter signals, which may be further processed (e.g., edge enhancement, logarithmic compression) into vector data values by the B-flow circuit 251 for the scan converter 292 (e.g., at 308).

The filter of the B-flow circuit 251 may correspond to a dedicated hardware device, such as an application specific integrated circuit. Additionally or alternatively, the B-flow circuit 251 may include one or more processors, a central controller circuit (CPU), and/or the like that execute instructions stored on the memory 140 to perform the filtering of the beam summed signals.

The filter of the B-flow circuit 251 may perform decoding, bandpass filtering and wall filtering based on a selection of filter coefficients. For example, the filter may include a finite impulse response (FIR) filter, which receives a first set of filter coefficients for filtering the receive beam summed signal produced as a result of a first coded transmit firing (e.g., at N=1), and receives a second set of filter coefficients for filtering the receive beam summed signal produced as a result of a second coded transmit firing (e.g., at N=2). The first set of filter coefficients may be formed by multiplying each of a predetermined set of filter coefficients by a first filter weighting (e.g., scaler value). The second set of filter coefficients is formed by multiplying each of the predetermined set of filter coefficients by a second filter weighting. The transmit phases and the filter weightings may be based or a function of generating the B-flow ultrasound imaging.

The FIR filter may have M filter taps for receipt of a respective set of M filter coefficients for each transmit firing. The filter coefficients for the n-th transmit firing may be $a_n c_1$, $a_n c_2$, ..., $a_n c_M$, where $a_n$ is the filter weighting for the n-th transmit firing, n=1, 2, ..., N, and where $c_1, c_2, ..., c_M$ is a set of filter coefficients selected to enable the FIR filter to compress the beam summed signals and passes a major fraction of the desired fundamental frequency band.

For example, the filter coefficients $c_1, c_2, ..., c_M$ are obtained by convolving a first set of filter coefficients $b_1, b_2, ..., b_P$ which are based on a desired frequency band, with a second set of filter coefficients $d_1, d_2, ..., d_Q$, which are either matched (e.g., same as the transmit code) or mismatched filter coefficients with respect to the transmit code, where M=(P+Q−1). The filter weightings $a_1, a_2, ..., a_N$ may function as a "wall" filter, which selectively passes signals from tissue (e.g., blood flow) moving at a velocity greater than a predetermined threshold. For example, the filter coefficients may be chosen to reject low frequencies which correspond to motion or velocities at low speeds.

The filter coefficients $a_n c_1$, $a_n c_2$, ..., $a_n c_M$ may be stored on the memory 290 and/or the memory 140. Select filter coefficients may be selected by the B-flow circuit 251 for each transmit firing by the transducer elements 124. For example, for the first transmit firing, the B-flow circuit 251 may select the filter coefficients $a_1 c_1, a_1 c_2, ..., a_1 c_M$ from the filter coefficients $a_n c_1, a_n c_2, ..., a_n c_M$ stored on the memory 290 for the filter, for the second transmit firing, the B-flow circuit 251 may select the filter coefficients $a_2 c_1$, $a_2 c_2, ..., a_n c_M$ for the filter, and/or the like. Additionally or alternatively, the controller circuit 136 may adjust filter coefficients based on a diagnostic application selected by the user via the user interface 142. Optionally, different sets of filter coefficients may be stored in lookup tables in the memory 290 and the desired set of coefficients may be selectable by the user and/or automatically selected by the controller circuit 136.

At 308, the controller circuit 136 may generate an ultrasound image having tissue elements and blood elements of a region of interest (ROI) with the blood elements having a higher intensity than the tissue elements based on the filtered signals, such as a B-flow ultrasound image. For example, the filtered signals associated with the coded excitations may be processed (e.g., edge enhancement, logarithmic compression) by the B-flow circuit 251 or generally the controller circuit 136 into vector data values for the B-flow ultrasound image, which are stored on the memory 290. The scan converter 292 accesses and obtains from the memory 290 the vector data values for the B-flow ultrasound image and converts the set of vector data values to Cartesian coordinates to generate the B-flow ultrasound image frames formatted for display. The generated B-flow ultrasound images may be stored in the memory 290 to be accessed by the display circuit 298 and/or for further processing (e.g., segmentation).

The B-flow ultrasound image includes tissue elements and blood elements. For example, the tissue elements may correspond to pixels or voxels of the B-flow ultrasound image of tissue structures of the ROI. The blood elements may correspond to pixels or voxels of the B-flow ultrasound image of blood flowing within the ROI. The blood elements of the B-flow ultrasound image have higher intensities or brightness relative to the tissue elements. For example, the B-flow ultrasound image may be of an ROI corresponding to a left ventricle of the patient. The tissue elements (e.g., pixels, voxels) corresponding to the endocardium surrounding the ROI will have a lower intensity or brightness than the blood elements (e.g., pixels, voxels) corresponding to blood flowing within the ROI.

It should be noted that although a B-flow modality is described with respect to 308, various other embodiments may utilize other modalities, such as a contrast enhanced ultrasound image (e.g., by injecting a contrast media such as gas-filled microbubbles or Optison into the ROI) or a Doppler color flow ultrasound image. For example, the color flow circuit 252 or generally the controller circuit 136 may generate an ultrasound image using a color-flow or Doppler modality by emitting Doppler signals or pulse trains from the transducer elements 124, and calculating a Doppler shift between the pulse trains and at least a portion of the Doppler signals back scattered from the ROI. In another example, the contrast enhanced circuit 264 or generally the controller circuit 136 may generate an ultrasound image based on a contrast enhanced modality.

At 310, the controller circuit 136 generates an ultrasound image having tissue elements and blood elements of the ROI with the tissue elements having a higher intensity than the blood elements, such as a B-mode ultrasound image. The B-mode image may be based on the received signals associated with the uncoded excitation or the filtered signals of the coded excitations (e.g., based on the same acquisition/transmit signals used for the B-flow image at 308). In various embodiments, the B-mode ultrasound image may be a (sub)harmonic or fundamental image based on the received signals resulting by the uncoded excitations or pulses transmitted by the transducer elements 124 at, for example, $f_0$ (usually the transducer lower frequency band edge). The received signals associated with the uncoded excitation may be included in the ultrasound data 270 (FIG. 2) received by the B-mode circuit 256 as the ultrasound data 270. Optionally, the B-mode circuit 251 may include a filter, such as a bandpass filter centered at frequency $2f_0$ (second harmonic) or frequency $f_0/2$ (subharmonic). The B-mode circuit 256 or generally the controller circuit 136 may calculate vector data values from the received signals for the B-mode ultrasound image, which are stored on the memory 290.

The scan converter 292 accesses and obtains from the memory 290 the vector data values for the B-mode ultrasound image and converts the set of vector data values to Cartesian coordinates to generate the B-mode ultrasound image frames formatted for display. The generated B-mode ultrasound images may be stored in the memory 290 to be accessed by the display circuit 298 and/or for further processing (e.g., segmentation).

Figure 4:
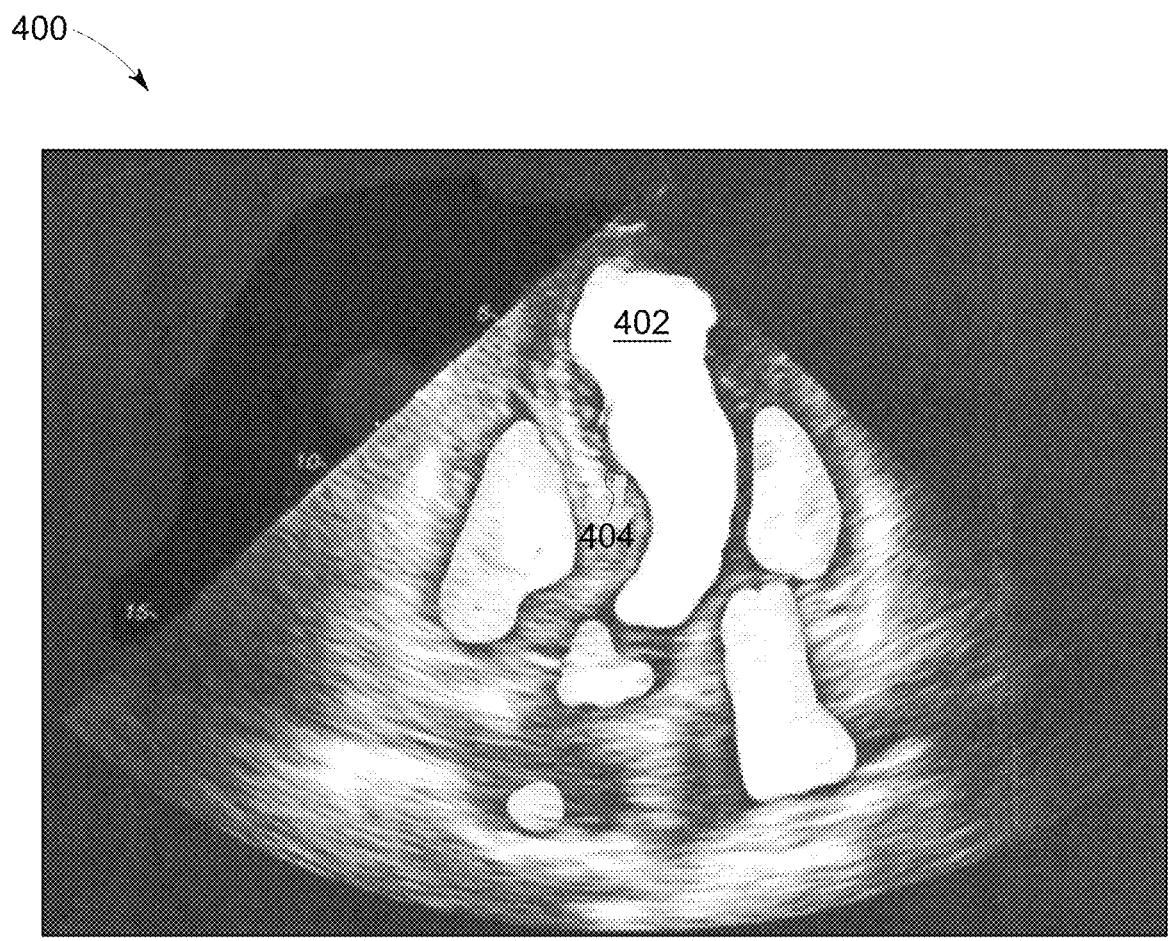
FIG. 4 is an illustration of a B-flow ultrasound image overlaid on a B-mode ultrasound image, in accordance with an embodiment.

The B-flow ultrasound image and the B-mode ultrasound image may be displayed individually (e.g., side-by-side) on the display 138. Additionally or alternatively, in connection with FIG. 4, the B-flow ultrasound image may be overlaid on the B-mode ultrasound image to form an ultrasound image 400. The ultrasound image 400 may allow the user to observe the flow of blood (e.g., based on the B-flow ultrasound image), for example within an ROI 402 corresponding to a left ventricle, relative to known anatomical landmarks (e.g., based on the B-mode ultrasound image), for example an endocardium 404, during medical diagnosis.

At 312, the controller circuit 136 may perform segmentation to the B-mode and B-flow ultrasound images for the ROI. In connection with FIG. 5, the controller circuit 136 may perform the segmentation by simultaneously applying edge detection to the B-mode and B-flow ultrasound images for the ROI.

Figure 5:
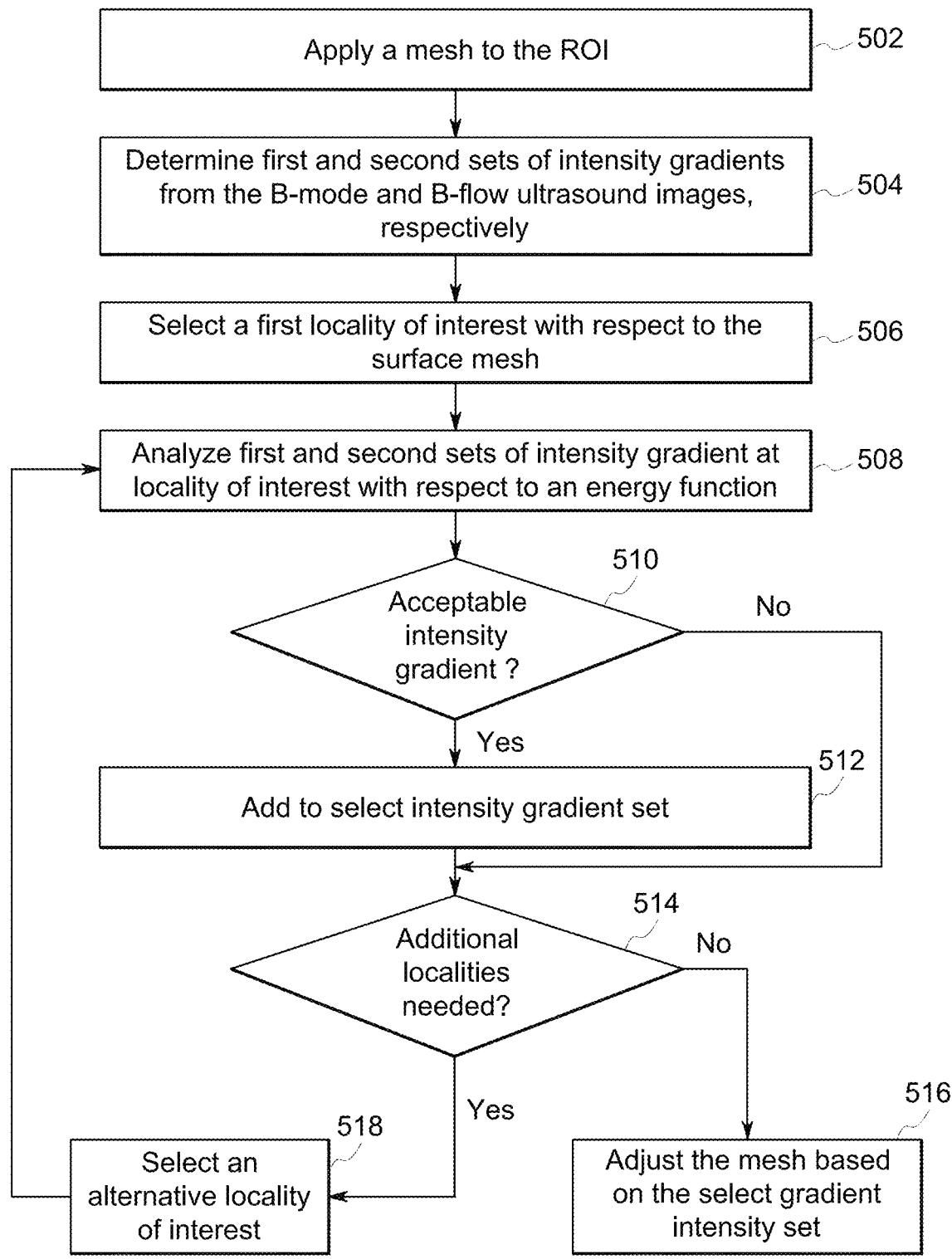
FIG. 5 illustrates a flowchart of a method for performing segmentation by simultaneously applying edge detection to a B-flow ultrasound image and a B-mode ultrasound image for a region of interest, in accordance with an embodiment.

FIG. 5 is a flowchart for performing segmentation by simultaneously applying edge detection to the B-flow ultrasound image and the B-mode ultrasound image. The method, for example, may correspond to operations performed by the controller 136 by executing one or more algorithms stored in memory (e.g., the memory 140, the memory 290). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be used as one or more algorithms to direct hardware to perform one or more operations described herein. It should be noted, other methods may be used, in accordance with embodiments herein.

Beginning at 502, the controller circuit 136 may apply a mesh 602 to the ROI 402. In connection with FIG. 6, the mesh 602 may have an initial size and/or shape based on a mesh template database stored in the memory 140. The mesh template database may be a collection of candidate meshes with corresponding anatomical structures.

For example, the user may select and/or designate the ROI 402 by selecting a structure within the B-mode ultrasound image and/or the B-flow ultrasound image via the user interface 142. Additionally or alternatively, the user may designate the ROI 402 based on a diagnostic selection (e.g., cardiac output measurement) for the ultrasound imaging system 100. The ROI 402 may correspond to a cardiac structure such as a left ventricle, a right ventricle, a left atrium, a right atrium, a left ventricular outflow tract, and/or the like. Based on the selection of the ROI 402 the controller circuit 136 may compare the cardiac structure represented by the ROI 402 with the collection of candidate meshes in the mesh template database. The controller circuit 136 may select one of the candidate meshes that match the anatomical structure of the ROI 402 and overlay the mesh 602 on the ROI 402. Optionally, the user may adjust a shape the mesh 602 and/or reposition the mesh 602 via the user interface 142.

Figure 6:
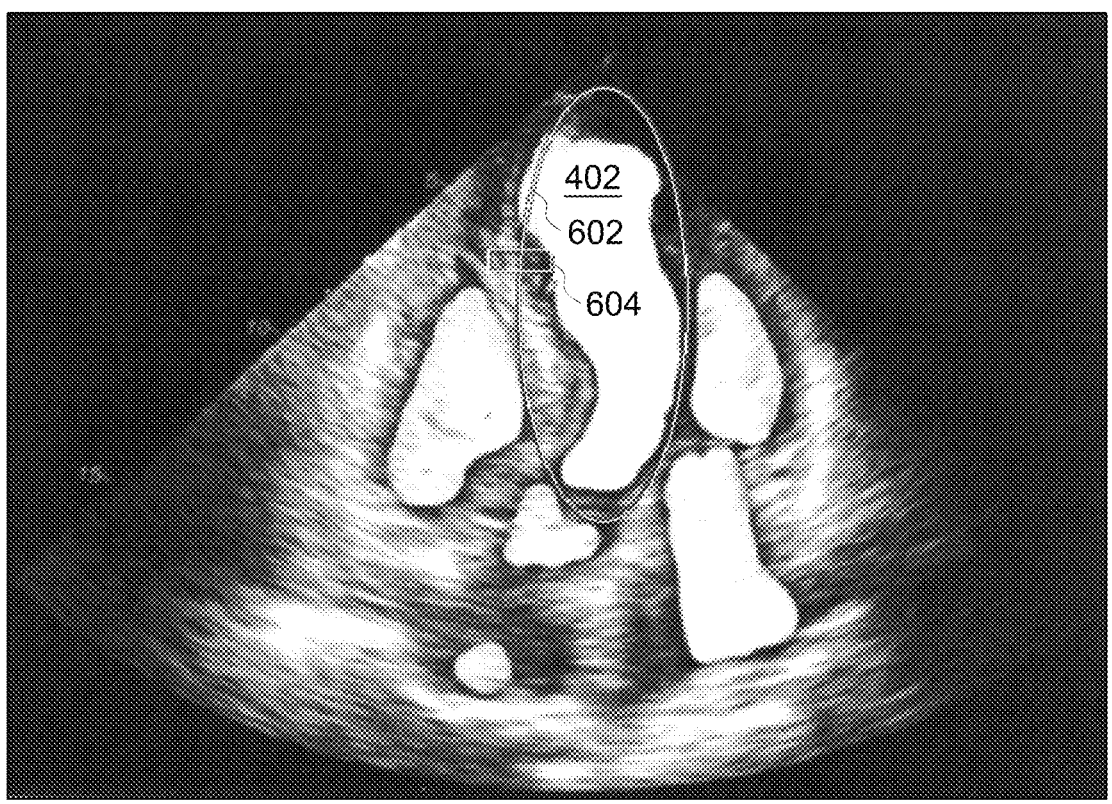
FIG. 6 is an illustration of a mesh applied to a region of interest, in accordance with an embodiment.

FIG. 6 is an illustration of the mesh 602 being applied to the ROI 402 shown by the ultrasound image 400. The mesh 602 may be subdivided into a plurality of surface patches, for example, the mesh 602 may be based on a Doo-Sabin surface, a Catmull-Clark surface, an active contour, a level set, a B-spline, and/or the like. The surface patches are repositionable allowing the controller circuit 136 and/or user via the user interface 142 to adjust a shape of the mesh 602. For example, adjusting a position of one or more surface patches to conform a topology or overall shape of the mesh 602 to locations of edges of the ROI 402 as described in connection to 516 of FIG. 5. It should be noted that although the mesh 602 is shown in 2D, in various other embodiments a 3D mesh 602 may be applied by the controller circuit 136.

Additionally or alternatively, each surface patch is movable along a surface patch axis. For example, controller circuit 136 may define a surface point at a central position for each surface patch. The controller circuit 126 may calculate the surface patch axis along surface normal vectors extending perpendicular relative to the opposing surfaces of each surface patch from the corresponding surface point.

Returning to FIG. 5, at 504 the controller circuit 136 may determine first and second sets of intensity gradients from the B-mode and B-flow ultrasound images, respectively. The first and second sets of intensity gradients may be collections of calculated intensity gradient vectors or intensity gradient magnitudes corresponding to locations (e.g., along the surface patch axes) of the B-mode ultrasound image and the B-flow ultrasound image, respectively. For example, the controller circuit 136 may calculate a derivative of the B-mode ultrasound image (for the first set) corresponding to a change in pixel intensity (or voxels for 3D ultrasound images) proximate to and/or around the mesh 602 along each surface patch axis within a set distance threshold.

At 506, the controller circuit 136 may select a locality of interest 604 with respect to the mesh 602. The locality of interest 604 may correspond to an area of pixels from the B-mode ultrasound image and the B-flow ultrasound image based on one of the surface patches of the mesh 602. For example, the locality of interest 604 may be a series of pixels extending a predetermined distance along a surface patch axis of one of the surface patches. Additionally or alternatively, the locality of interest 604 may be selected by the user via the user interface 142.

At 508, the controller circuit 136 analyzes the first and second sets of intensity gradients at the locality of interest 604 with respect to an energy function. The energy function may correspond to a machine learning algorithm stored in the memory 140 for selecting intensity gradients that correspond to an edge of an anatomical structure. The energy function may analyze one or more morphology characteristics of the intensity gradients to identify a location of an edge of the ROI 402.

For example, the energy function may include a gradient threshold, a location variance threshold, a peak form template and/or the like to determine from the first and second sets of intensity gradients a select intensity gradient set that correspond to the edge of the ROI 402. The gradient threshold may correspond to a peak value of a set of intensity gradients, such as a gradient magnitude, that indicates changes in adjacent pixel intensities representing an edge of the ROI 402. For example, a peak within a set of intensity gradients that is above the gradient threshold may indicate an edge. The location variance threshold may correspond to a distance threshold between peaks identified by the first and second set of intensity gradients. For example, only peaks of the first and second set of intensity gradients that are within the location variance threshold with respect to each other may indicate an edge of the ROI 402. The peak form template may correspond to an overall shape of a peak that indicates an edge. For example, the peak form template may define a slope thresholds and/or peak threshold values which define a peak that corresponds to an edge of the ROI 402.

Figure 7:
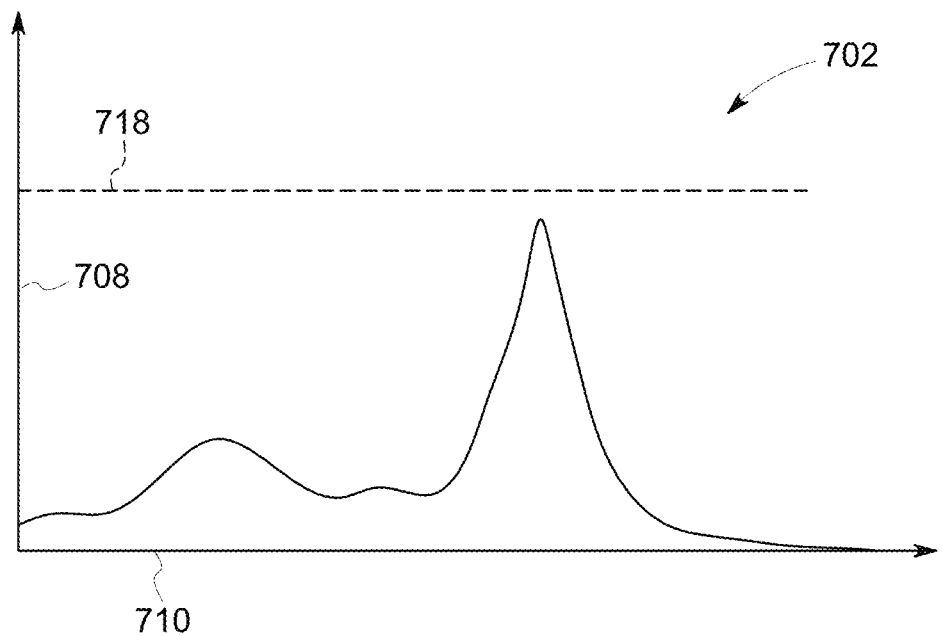
FIG. 7 is a graphical illustration of a first and second gradient set, in accordance with an embodiment.
Figure 7:
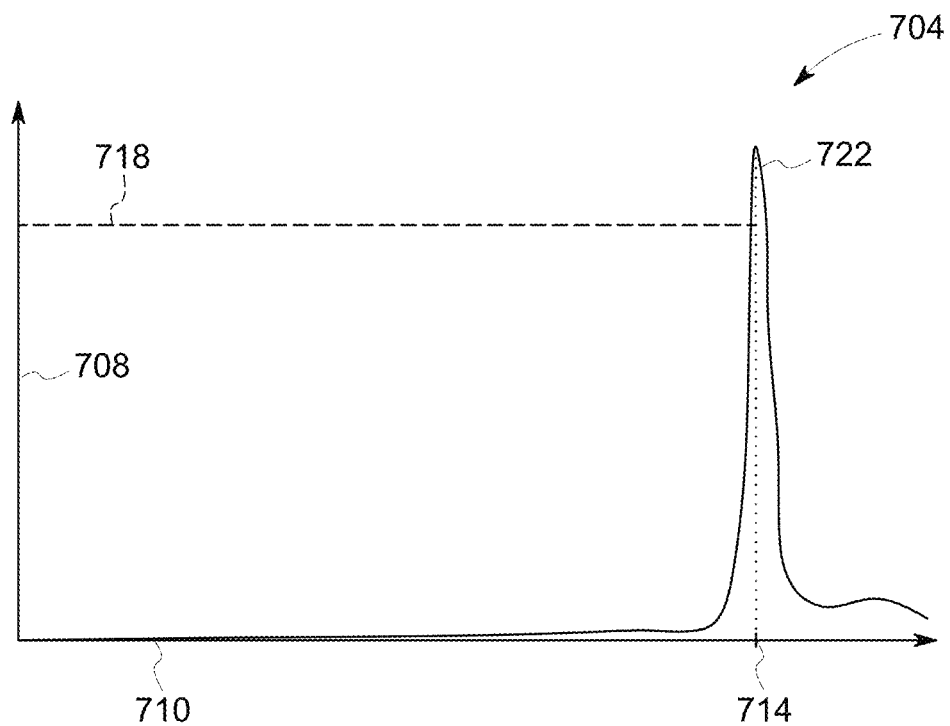

At 510, the controller circuit 136 may determine whether intensity gradients from the first and second sets correspond to an edge of the ROI 402 based on edge locations identified by the energy function. FIG. 7 is a graphical representation of a first set of intensity gradients 702 and a second set of intensity gradients 704 at the locality of interest 604, in accordance with an embodiment. The vertical axis 708 represents a magnitude of the intensity gradient, and the horizontal axis 710 corresponds to pixel locations with respect to the locality of interest 604. The controller circuit 136, when executing the energy function, may compare the first and second sets of intensity gradients 702 and 704 with the gradient threshold 718 to locate peaks of the first and second sets of intensity gradients 702 and 704 having intensity gradients above the gradient threshold 718, which identifies an edge of the ROI 402.

Intensity gradients identified by the controller circuit 136 that correspond to an edge of the ROI 402 may be added to a select intensity gradient set, at 512. For example, the controller circuit 136 may determine that the peak 722 of the second set 704 represents a pixel location 714 of the locality of interest 604 corresponding to an edge of the ROI 402. The controller circuit 136 may include the pixel location 714 to the select intensity gradient set, which indicates a location of the edge of the ROI 402 with respect to the locality of interest 604 (e.g., the surface patch). It should be noted, that in various embodiments the select intensity gradient set may include portions of the first and second sets of intensity gradients. For example, the energy function may locate an edge in the first set of intensity gradient and/or the second set of intensity gradients.

In various embodiments, the controller circuit 136 may determine different pixel locations of the locality of interest 604 that correspond to an edge of the ROI 402. Based on the different pixel locations, the controller circuit 136 may assimilate and/or adjust the pixel locations determined from the first and second set. For example, the controller circuit 136 may determine a first pixel location from the first set of intensity gradients (e.g., from the B-mode ultrasound image) and a second pixel location from the second set of intensity gradients (e.g., from the B-flow ultrasound image). The controller circuit 136 may calculate an average pixel location from the first and second pixel locations, which will be included by the controller circuit 136 to the select intensity gradient set.

At 514, the controller circuit 136 determines whether additional localities of interest need to be selected. For example, the controller circuit 136 may continue to select a new locality of interest, at 518, corresponding to a surface patch of the mesh 602 until each surface patch has a select intensity gradient corresponding to an edge of the ROI 402.

At 516, if no additional localities of interest are needed, the controller circuit 136 may adjust the mesh 602 based on the select gradient intensity set.

Figure 8:
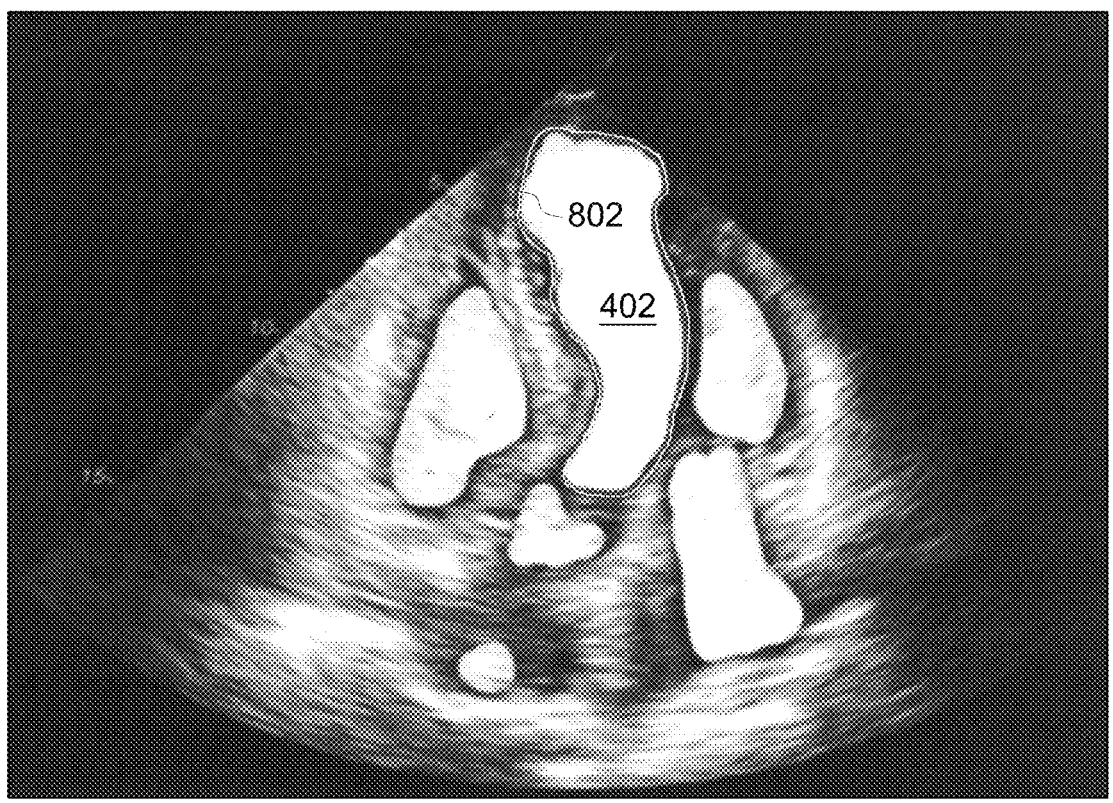
FIG. 8 is an illustration of an adjusted mesh based on a select gradient intensity set, in accordance with an embodiment.

FIG. 8 is an illustration of an adjusted mesh 802 based on the select gradient intensity set and the mesh 602. For example, the pixel locations of the select gradient intensity set may be used by the controller circuit 136 to reposition surface patches to the edge of the ROI 402 thereby adjusting the mesh 602. The controller circuit 136 may determine a distance between the pixel location 714 and the surface patch represented by the locality of interest 604 along the surface patch axis. The controller circuit 136 may adjust the surface patch by displacing the surface patch and/or projecting the surface point of the surface patch to the pixel location 714 along the surface patch axis.

Based on the adjusted mesh 802, the controller circuit 136 may segment the ROI 402 from the B-mode ultrasound image and/or the B-flow ultrasound image. Additionally or alternatively, the controller circuit 136 and/or user may perform diagnostic measurements (e.g., volume) based on the size of the ROI 402 defined by the mesh 802.

It should be noted in various embodiments other techniques may be used for segmentation to the B-mode and B-flow ultrasound images at 312 than described in connection with FIG. 5. For example, a step function having a 1D-intensity profile may be fitted (e.g., normal to the mesh) to determine simultaneously edges of the B-mode and the B-glow ultrasound images. In another example, the energy function may be applied to the B-mode and the B-flow ultrasound images describing certain statistical characteristics of the pixel data (e.g. mean, variance) to identify edges of the B-mode and the B-flow ultrasound images.

Additionally or alternatively, one or more operations (e.g., 302-312) of the method 300 may be performed remotely (e.g., at different location) and/or temporally offset using a workstation communicatively coupled to the ultrasound imaging system 100. For example, the user may access the B-mode and the B-flow ultrasound image stored on the memory 140 and/or the memory 290 acquired during a previous scan, in connection with 302-310, from a workstation communicatively coupled to the ultrasound imaging system 100. The user may perform access and/or select the B-mode and the B-flow ultrasound image to perform, at 312, the segmentation of the B-mode and the B-flow ultrasound images for the ROI.

Figure 9:
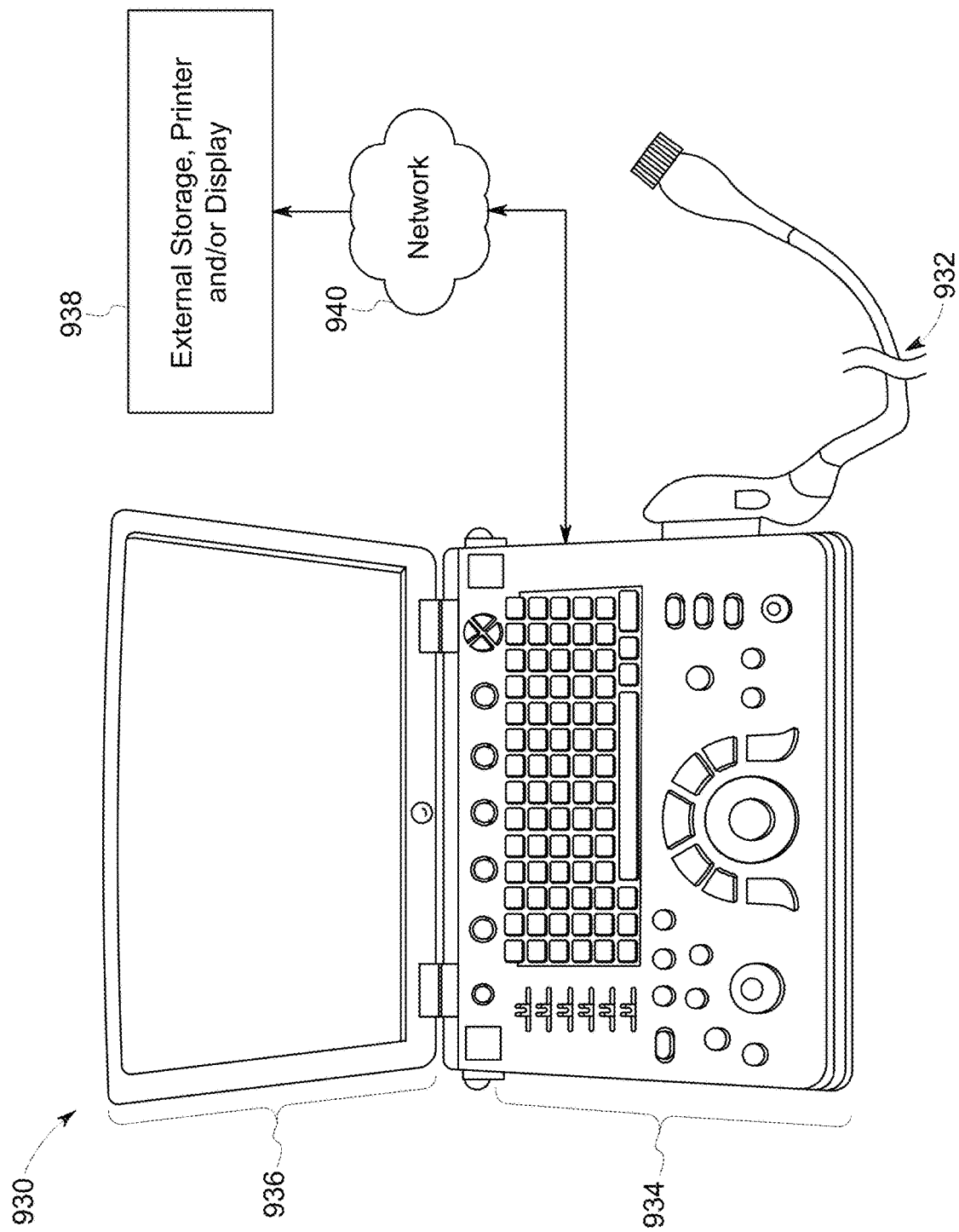
FIG. 9 illustrates a 3D capable miniaturized ultrasound system having a probe that may be configured to acquire 3D ultrasonic data or multi-plane ultrasonic data.
Figure 10:
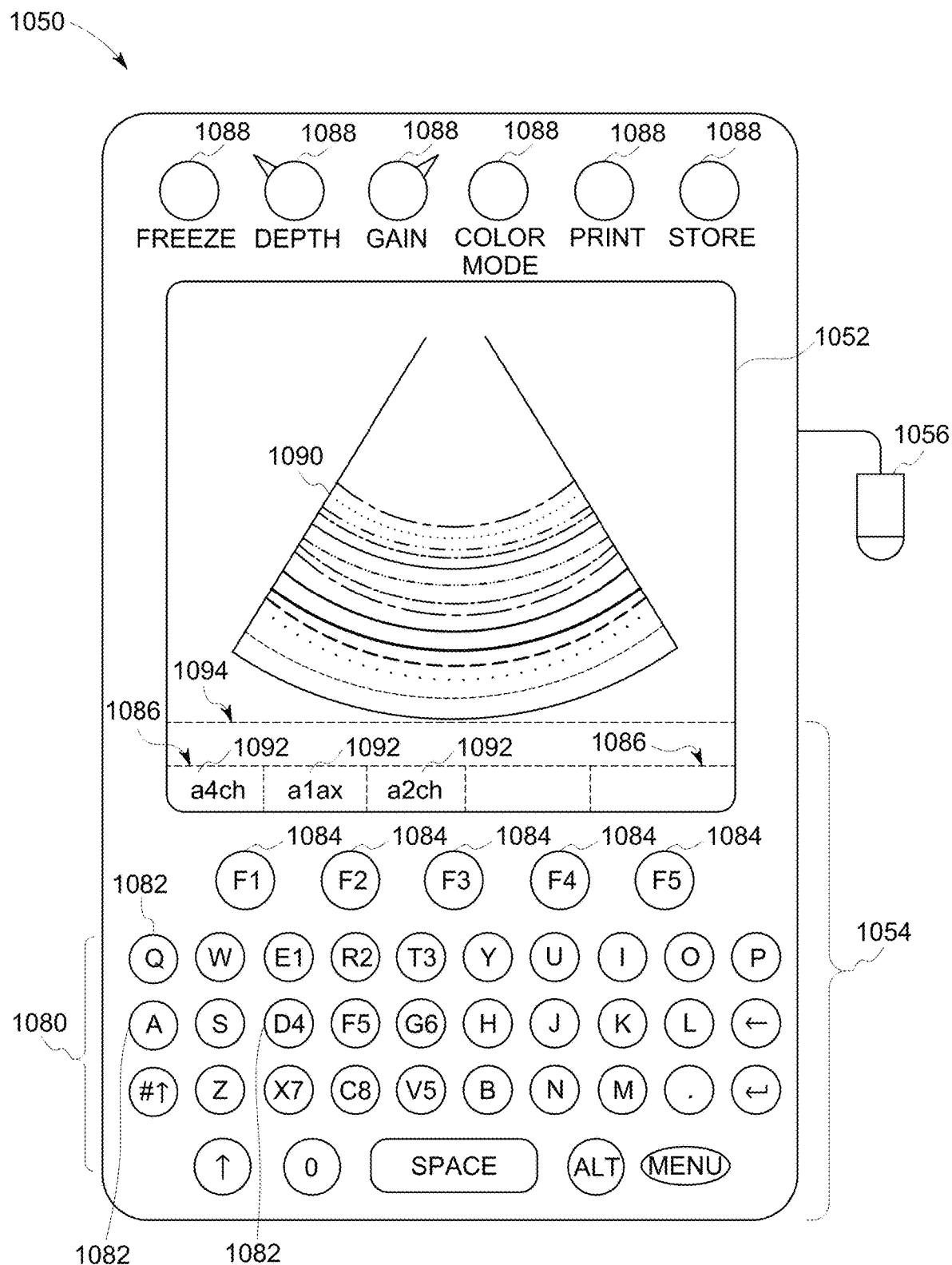
FIG. 10 illustrates a hand carried or pocket-sized ultrasound imaging system wherein the display and user interface form a single unit.
Figure 11:
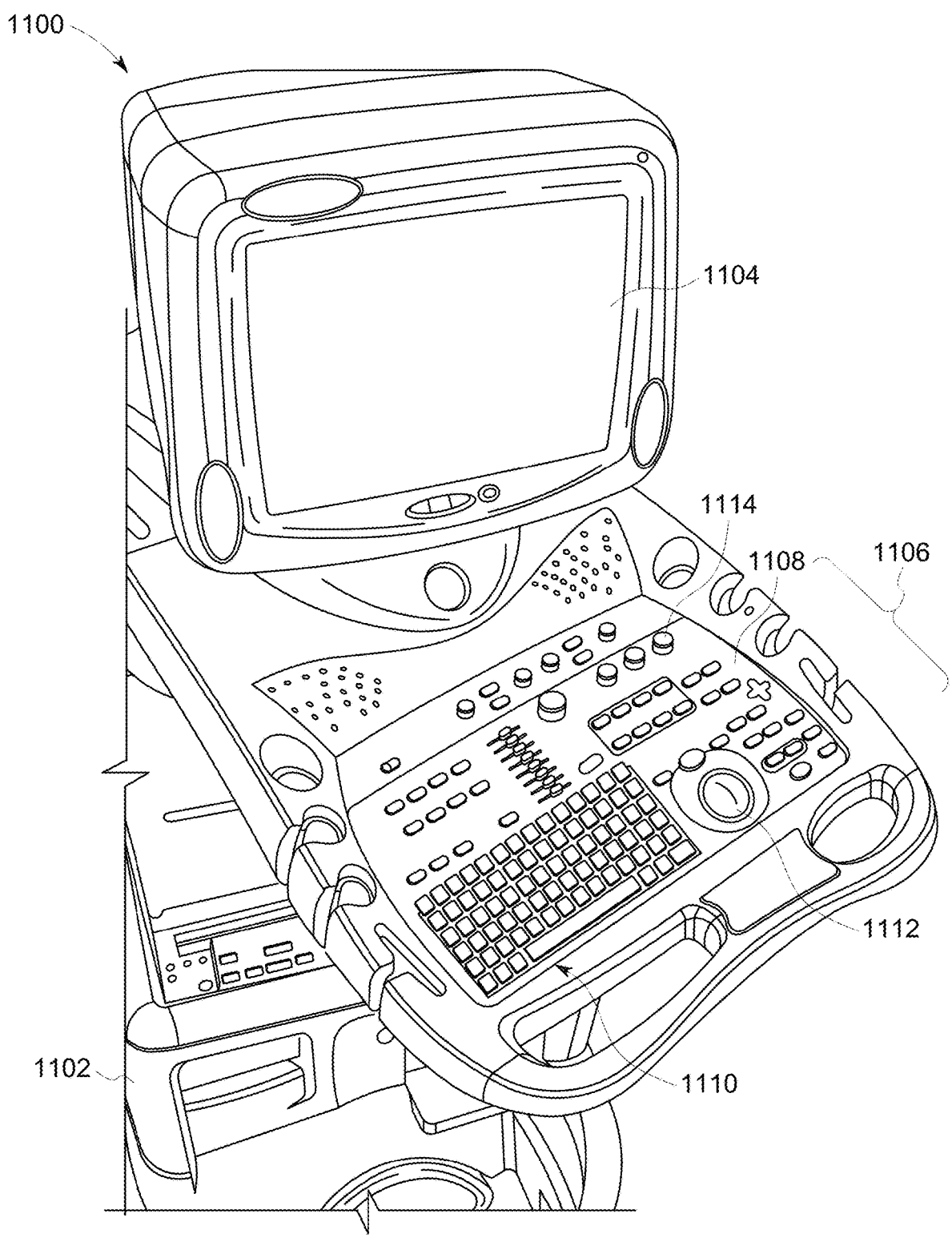
FIG. 11 illustrates an ultrasound imaging system provided on a movable base.

The ultrasound system 100 of FIG. 1 may be embodied in a small-sized system, such as laptop computer or pocket-sized system as well as in a larger console-type system. FIGS. 9 and 10 illustrate small-sized systems, while FIG. 11 illustrates a larger system.

FIG. 9 illustrates a 3D-capable miniaturized ultrasound system 930 having a probe 932 that may be configured to acquire 3D ultrasonic data or multi-plane ultrasonic data. For example, the probe 932 may have a 2D array of elements as discussed previously with respect to the probe. A user interface 934 (that may also include an integrated display 936) is provided to receive commands from an operator. As used herein, "miniaturized" means that the ultrasound system 930 is a handheld or hand-carried device or is configured to be carried in a person's hand, pocket, briefcase-sized case, or backpack. For example, the ultrasound system 930 may be a hand-carried device having a size of a typical laptop computer. The ultrasound system 930 is easily portable by the operator. The integrated display 936 (e.g., an internal display) is configured to display, for example, one or more medical images.

The ultrasonic data may be sent to an external device 938 via a wired or wireless network 940 (or direct connection, for example, via a serial or parallel cable or USB port). In some embodiments, the external device 938 may be a computer or a workstation having a display. Alternatively, the external device 938 may be a separate external display or a printer capable of receiving image data from the hand carried ultrasound system 930 and of displaying or printing images that may have greater resolution than the integrated display 936.

FIG. 10 illustrates a hand carried or pocket-sized ultrasound imaging system 1050 wherein the display 1052 and user interface 1054 form a single unit. By way of example, the pocket-sized ultrasound imaging system 1050 may be a pocket-sized or hand-sized ultrasound system approximately 2 inches wide, approximately 4 inches in length, and approximately 0.5 inches in depth and weighs less than 3 ounces. The pocket-sized ultrasound imaging system 1050 generally includes the display 1052, user interface 1054, which may or may not include a keyboard-type interface and an input/output (I/O) port for connection to a scanning device, for example, an ultrasound probe 1056. The display 1052 may be, for example, a 320×320 pixel color LCD display (on which a medical image 1090 may be displayed). A typewriter-like keyboard 1080 of buttons 1082 may optionally be included in the user interface 1054.

Multi-function controls 1084 may each be assigned functions in accordance with the mode of system operation (e.g., displaying different views). Therefore, each of the multi-function controls 1084 may be configured to provide a plurality of different actions. One or more interface components, such as label display areas 1086 associated with the multi-function controls 1084 may be included as necessary on the display 1052. The system 1050 may also have additional keys and/or controls 1088 for special purpose functions, which may include, but are not limited to "freeze," "depth control," "gain control," "color-mode," "print," and "store."

One or more of the label display areas 1086 may include labels 1092 to indicate the view being displayed or allow a user to select a different view of the imaged object to display. The selection of different views also may be provided through the associated multi-function control 1084. The display 1052 may also have one or more interface components corresponding to a textual display area 1094 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 1050 and the miniaturized ultrasound system 930 may provide the same scanning and processing functionality as the system 100.

FIG. 11 illustrates an ultrasound imaging system 1100 provided on a movable base 1102. The portable ultrasound imaging system 1100 may also be referred to as a cart-based system. A display 1104 and user interface 1106 are provided and it should be understood that the display 1104 may be separate or separable from the user interface 1106. The user interface 1106 may optionally be a touchscreen, allowing the operator to select options by touching displayed graphics, icons, and the like.

The user interface 1106 also includes control buttons 1108 that may be used to control the portable ultrasound imaging system 1100 as desired or needed, and/or as typically provided. The user interface 1106 provides multiple interface options that the user may physically manipulate to interact with ultrasound data and other data that may be displayed, as well as to input information and set and change scanning parameters and viewing angles, etc. For example, a keyboard 1110, trackball 1112 and/or multi-function controls 1114 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound imaging system, comprising:
a transducer array comprising a plurality of transducer elements;
a transmit circuit to drive the transducer array;
a receive beamformer to collect receive signals from the transducer array and to form beam summed signals; and
one or more processors and a memory for storing programmed instructions, wherein the one or more processors execute the programmed instructions by performing the following operations:
generate a first ultrasound image of a region of interest (ROI) having tissue elements and blood elements, wherein the tissue elements of the first ultrasound image have a higher intensity than the blood elements of the first ultrasound image;
generate a second ultrasound image of the ROI having tissue elements and blood elements, wherein the blood elements of the second ultrasound image have a higher intensity than the tissue elements of the second ultrasound image;
determine a first set of intensity gradients from the first ultrasound image and a second set of intensity gradients from the second ultrasound image;
locate an edge of the ROI using the first and second sets of intensity gradients; and
perform segmentation on the ROI from one or more of the first ultrasound image or the second ultrasound image based on the edge of the ROI.

2. The ultrasound imaging system of claim 1, wherein the one or more processors are configured to locate a blood-tissue interface as the edge based on the first set of intensity gradients and based on the second set of intensity gradients.

3. The ultrasound imaging system of claim 2, wherein the first ultrasound image corresponds to a B-mode ultrasound image, and the second ultrasound image corresponds to a B-flow ultrasound image, a Doppler color flow ultrasound image, or a contrast enhanced ultrasound image.

4. The ultrasound imaging system of claim 2, wherein the one or more processors further apply a mesh to the ROI and adjust a shape of the mesh based on the edge of the ROI.

5. The ultrasound imaging system of claim 4, wherein the mesh is selected by the one or more processors from a plurality of candidate meshes stored on the memory based on a diagnostic selection.

6. The ultrasound imaging system of claim 1, wherein the one or more processors are configured to locate the edge of the ROI by applying an energy function to the first and second sets of intensity gradients to determine a select intensity gradient set corresponding to the edge of the ROI.

7. The ultrasound imaging system of claim 6, wherein the energy function includes a gradient threshold or a location variance threshold.

8. The ultrasound imaging system of claim 6, wherein the select intensity gradient set includes portions of the first and second sets.

9. The ultrasound imaging system of claim 1, wherein the one or more processors overlay the first ultrasound image on the second ultrasound image.

10. A method for segmenting a structure comprising:
driving a plurality of transducer elements;
collecting receive signals from the transducer array at a receive beamformer to form beam summed signals;
generating a first ultrasound image of a region of interest (ROI) having tissue elements and blood elements, wherein the tissue elements of the first ultrasound image have a higher intensity than the blood elements of the first ultrasound image;
generating a second ultrasound image of the ROI having tissue elements and blood elements, wherein the blood elements of the second ultrasound image have a higher intensity than the tissue elements of the second ultrasound image;
determining a first set of intensity gradients from the first ultrasound image and a second set of intensity gradients from the second ultrasound image;
applying an energy function to the first and second sets of intensity gradients to locate an edge of the ROI; and
performing segmentation on the ROI from one or more of the first ultrasound image or the second ultrasound image based on the edge of the ROI.

11. The method of claim 10, wherein applying the energy function to the first and second sets of intensity gradients to locate the edge of the ROI includes locating a blood-tissue interface as the edge based on the first set of intensity gradients and based on the second set of intensity gradients.

12. The method of claim 11, wherein the first ultrasound image corresponds to a B-mode ultrasound image, and the second ultrasound image corresponds to a B-flow ultrasound image, a Doppler color flow ultrasound image, or a contrast enhanced ultrasound image.

13. The method of claim 11, further comprising:
applying a mesh to the ROI; and
adjusting a shape of the mesh based on the edge of the ROI for the segmentation operation.

14. The method of claim 10, wherein the energy function includes a gradient threshold or a location variance threshold.

15. The method of claim 10, wherein applying the energy function to the first and second sets of intensity gradients includes compiling intensity gradients from the first and second sets that correspond to the edge of the ROI into a select intensity gradient set.

16. A tangible and non-transitory computer readable medium comprising one or more computer software modules configured to direct one or more processors to:
drive a plurality of transducer element;
collect receive signals from the transducer array at a receive beamformer to form beam summed signals;
generate a first ultrasound image of a region of interest (ROI) having tissue elements and blood elements, wherein the tissue elements of the first ultrasound image have a higher intensity than the blood elements of the first ultrasound image;
generate a second ultrasound image of the ROI having tissue elements and blood elements, wherein the blood elements of the second ultrasound image have a higher intensity than the tissue elements of the second ultrasound image;
determine a first set of intensity gradients from the first ultrasound image and a second set of intensity gradients from the second ultrasound image;
locate an edge of the ROI using the first and second sets of intensity gradients; and
perform segmentation on the ROI from one or more of the first ultrasound image or the second ultrasound image based on the edge of the ROI.

17. The tangible and non-transitory computer readable medium of claim 16, wherein the one or more processors are directed to locate a blood-tissue interface as the edge based on the first set of intensity gradients and based on the second set of intensity gradients.

18. The tangible and non-transitory computer readable medium of claim 17, wherein the one or more processors are further directed to:
apply a mesh to the ROI; and
adjust a shape of the mesh based on the edge of the ROI for the segmentation operation.

19. The tangible and non-transitory computer readable medium of claim 16, wherein the one or more processors are directed to locate the edge of the ROI by applying an energy function to the first and second sets of intensity gradients to determine a select intensity gradient set corresponding to the edge of the ROI.

20. The tangible and non-transitory computer readable medium of claim 17, wherein the first ultrasound image corresponds to a B-mode ultrasound image, and the second ultrasound image corresponds to a B-flow ultrasound image, a Doppler color flow ultrasound image, or a contrast enhanced ultrasound image.

21. The tangible and non-transitory computer readable medium of claim 19, wherein the energy function that is applied analyzes morphology characteristics of the intensity gradients in both the first and second sets to locate the edge of the ROI.

* * * * *